United States Patent [19]

Moore

[11] 4,297,640

[45] Oct. 27, 1981

[54] APPARATUS FOR MEASURING THE ELECTRIC CHARGE CONDITION OF NON-CONDUCTIVE PARTICLES IN A MILDLY CONDUCTIVE ELECTROLYTE

[75] Inventor: Zack J. Moore, Lake Jackson, Tex.

[73] Assignee: The Dow Chemical Company, Midland, Mich.

[21] Appl. No.: 120,405

[22] Filed: Feb. 11, 1980

[51] Int. Cl.³ ............................................. G01R 5/28
[52] U.S. Cl. .................................................... 324/458
[58] Field of Search ................ 324/71 CP, 425, 439, 324/447, 449, 450; 204/195 R

[56] References Cited

U.S. PATENT DOCUMENTS

| | | | |
|---|---|---|---|
| 3,365,376 | 1/1968 | Weyland | 324/447 |
| 3,368,144 | 2/1968 | Gerdes | 324/458 |
| 3,368,145 | 2/1968 | Gerdes | 324/458 |
| 3,369,984 | 2/1968 | Gerdes | 204/195 |
| 3,993,945 | 11/1976 | Warmoth | 324/449 |

*Primary Examiner*—Michael J. Tokar
*Attorney, Agent, or Firm*—M. W. Barrow

[57] ABSTRACT

The addition of a grounded electrode in a special location with respect to the location of the two sensing electrodes of an existing piston-inverted cylinder apparatus used in the measurement of the electric charge condition of non-conductive particles suspended in a mildly conductive electrolyte such as tap water converts the known apparatus into one whose accuracy, reliability and useful life are greatly increased. The grounded electrode is located nearer the open end of the cylinder than are the two sensing electrodes, and the grounded electrode should have a surface area which is several times that of the two sensing electrodes. All three electrodes must be made of the same metal.

3 Claims, 1 Drawing Figure

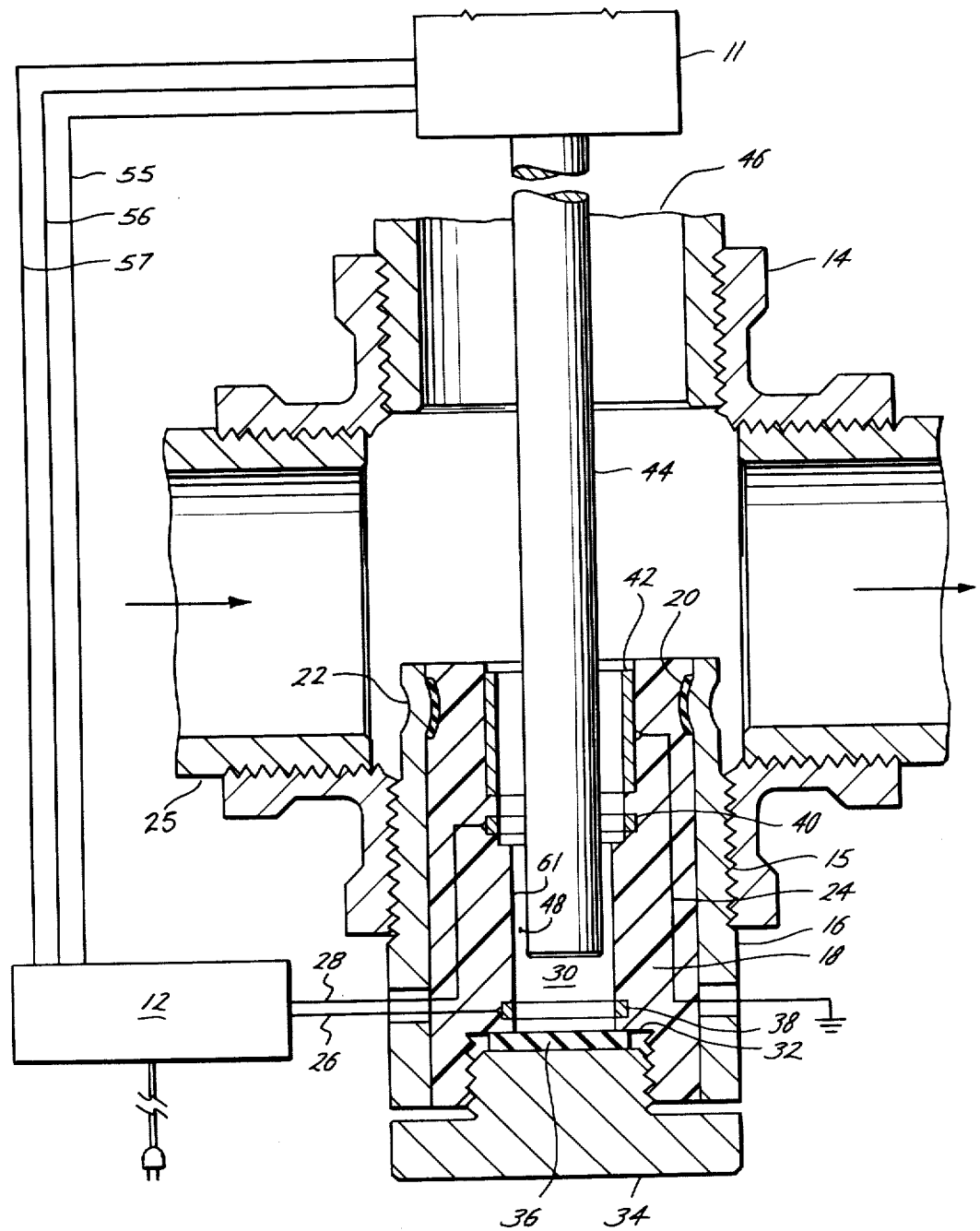

APPARATUS FOR MEASURING THE ELECTRIC CHARGE CONDITION OF NON-CONDUCTIVE PARTICLES IN A MILDLY CONDUCTIVE ELECTROLYTE

BACKGROUND OF THE INVENTION

This invention relates to the improvement of an apparatus useful for continuously measuring the electrical charge condition of electrically nonconductive, but electrically charged, particles suspended in a supporting liquid such as water. For example, this apparatus can continuously measure the charge concentration of the silt suspended in river water, used in industrial processes or the charge concentration of particles suspended in sewage.

Usually it is desirable to remove such suspended particles before using them in industrial processes. This is often accomplished by adding flocculating agents of opposite electric charge. The flocs thus formed are then readily removed by such methods as sedimentation, filtration, flotation, centrifugation and the like. One problem, of course, in adding such flocculating agents, is knowing which type of charged agent to add, that is negatively or positively charged agents. A second problem is to know how much of such agent should be added. Adding too little does not result in the maximum flocculation and suspended particle removal. On the other hand adding too much flocculating agent can result in shifting the electrical imbalance too far which may contribute to the suspension stability thus having an undesirable effect. Thus in streams such as river water flowing continuously into industrial plants wherein it is highly desirable to remove the suspended solids therefrom, it is highly desirable to be able to measure accurately the charge concentration of the non-conductive suspended particles even though the concentration varies so that the exact amount of the correctly charged flocculating agent can be added to the stream.

A partially successful attempt at making an apparatus which sould make such continuous measurements is disclosed in W. F. Gerdes U.S. Pat. No. 3,368,145, issued on Feb. 6, 1968, and incorporated herein by reference. This prior art apparatus, for which the present invention is an improvement, measures this particle charge conditions by measuring the streaming current (electrical) of the liquid suspension as it is swiftly forced past two spaced electrodes located in a substantially vertical, but inverted, piston and cylinder configuration. In this configuration both the interior of the cylinder wall and the external wall of the piston are electrically non-conductive, the cylinder is closed at its bottom and open at its top to allow entry and exit of the suspension sample being measured. The piston is fitted loosely enough within the cylinder so that when it is reciprocated within the cylinder the suspension sample is forced in and out of the cylinder between the walls of the piston and cylinder at a sufficiently fast velocity and under a sufficient pressure to ideally measure the streaming current of the suspension sample, and hence give an alternating electrical signal at the two electrodes which is a function of the charge concentration on the suspended particles within the sample. However, considerable difficulty has been met by trying to use this apparatus under field conditions. Erratic and erroneous measurements are often encountered after only a few hours field service.

It would be highly advantageous to eliminate these measurement errors and provide an apparatus which was accurate and stable over a long period of time in both the field and the lab. The present invention achieves this and other advantages.

SUMMARY OF THE INVENTION

A very stable, long-life accurate apparatus for measuring a streaming current and/or streaming potential of charged non-conductive particles suspended in a mildly conductive electrolyte can be synergistically achieved when the addition of a third, grounded electrode is added to the above discussed apparatus whose essence is disclosed in U.S. Pat. No. 3,368,145. That is such an apparatus can be achieved if this third, grounded electrode is located in proper relationship to the two sensing electrodes and the remainder of the apparatus, and if all three electrodes are made of the same metal.

More specifically a summary of this invention is as follows. The improved apparatus is useful in determining the electrical charge condition in a flowable liquid media containing a mildly conductive liquid electrolyte and electrical charge influencing species, particularly electrical charge influencing species which are electrically non-conductive themselves but on whose surfaces electrical charges collect. From U.S. Pat. No. 3,368,145, the old parts of this apparatus are known to comprise a tubular flow path member, or cylinder, open at one end and having electrically insulating walls. A pair of spaced, sensing electrodes made of the same metal with one of the electrodes is taught as being at least near the closed end of said flow member and the other being at least near the open end of said flow path member. A block-like reciprocating member, also with electrically insulating walls, is taught as being located at least partially within the tubular flow path member to cause liquid located therein to flow to and fro in the flow path member in a repetitive manner. Such a block-like member can be a piston loosely fitted and slidably mounted in said flow path member, or it can be a piston with lands slidably mounted in said flow path member. Means are taught as being coupled to said electrodes for amplifying and utilizing any electrical signal induced across said electrodes. The flow path member is disposed so that a continuously different sample of the flowable liquid media can be passed in and out of the cylinder in the space between the walls of the tubular flow path member and the walls of the block-like reciprocating member past the sensing electrodes.

The improvement of the present invention is the addition of a third electrode in the tubular flow path member This third electrode is grounded and preferably has a substantially larger surface area than the two sensing electrodes. This third electrode must be spaced from the two sensing electrodes, must be nearer the open end of the tubular flow path member than the two sensing electrodes, and must be made of the same metal as the two sensing electrodes. This arrangement prevents the sensing electrode formerly located "at or near the open end" of the flow path member in the prior art invention from being located there in this invention. Rather, now it must be located in the tubular flow path between the other sensing electrode and the third electrode. It is spaced from both.

It is preferred that this third electrode have a greater surface area exposed to the sample of liquid media flowing past it than the surface area of at least the sensing electrode located between it and the sensing electrode located nearest the closed end of the flow path member. Preferably the surface area and the electrical conductivity of the third electrode exposed to the flowable liquid media is much larger than the surface area of both sensing electrodes exposed to the flowable liquid media.

These and other features of the present invention may be more clearly observed by reference to the drawing and detailed description of the preferred embodiment of the present invention.

BRIEF DESCRIPTION OF THE DRAWING

The drawing is a partially diagrammatic, sectional elevation of an apparatus made in accordance with this invention.

DETAILED DESCRIPTION OF THE PREFERRED EMBODIMENT

Referring to FIG. 1, a four way metal pipe cross connection 14 can be observed. Annular metal pipe section 16 is screwed into the bottom of pipe, cross connection 14 via threads 15. A hollow, annular, electrically non-conductive plastic section 18 is tightly fitted into pipe section 16. The plastic used is Instant Set Polyurethane (herinafter ISP). A sealed fit between pipe section 16 and plastic section 18 is desired to prevent liquid from reaching electric wire conductive lines 24, 26 and 28. To assure this seal a small ring of Silastic* 20 is fitted between pipe section 16 and plastic section 18 at portion 22 of pipe section 16, and pipe section 16 is swaged inwardly at portion 22. Of course, Silastic plastic 20 is located between the tops fo the pipe and annular plastic sections 16 and 18 and the wire leads 24, 26 and 28.

*Trademark of The Dow Corning Corporation

ISP plastic section 18 has a hollow cylinder 30 in its center as well as a larger, hollow, threaded cylinder 32 in its lower portion. Polyvinyl plastic threaded plug 34 is screwed into threaded annular plastic section cylinder 32 to close the bottom of cylinder 30. Cylindrical cushion pad 36, made of rubber, has a larger diameter than cylinder 30 and is squeezed between the top of plug 34 and the bottom of cylinder 30 in order to assure a hydraulic seal between plastic section 18 and plastic section 34.

Inside of cylinder 30 are located three silver electrodes 38, 40, and 42. These electrodes 38, 40 and 42, are inset in the wall of cylinder 30. These three electrodes 38, 40, and 42, are thin cylindrical rings fitting around the wall of cylinder 30. Electrodes 38 and 40 are the sensing electrodes and have wire leads 26 and 28, respectively, leading through plastic section 18 and pipe section 16. Leads 26 and 28 exit from pipe section 16 inside a single, shielded cable (not shown) to prevent stray electrical interference radiation and stray electrical reactance from altering the very small electrical signals transmitted from sensing electrodes 38 and 40 through leads 28 and 26.

Electrodes 38, 40, and 42 are arranged as shown; i.e. sensing electrode 38 is located in the bottom of cylinder 30, sensing electrode 40 is located about two-thirds of the distance from the bottom of cylinder 30 to its top, and guard electrode 42 is located near the top of cylinder 30. All three of these electrodes are spaced apart along the interior of cylinder 30 thereby being electrically insulated from one another insofar as the non-conductive ISP plastic wall in which they are inset is concerned. They are thus left to be electrically connected by the liquid in the cylinder 30.

The new guard electrode 42 is the essence of the improvement to the existing apparatus. Preferably it has a surface area exposed to the interior of cylinder 30 which is about ten times as great as the surface areas of sensing electrodes 38 and 40 so that the electrical conductivity of guard electrode 42 is about ten times greater than sensing electrodes 38 and 40, and more particularly this conductivity is about ten times greater than the sensing electrode 40 nearest it. Preferably all three electrodes are made from silver.

It is necessary that guard electrode 42 be electrically grounded. This is accomplished by connecting electrode 42 to pipe section 16 via electrically conductive line 24. In the drawing, line 24 is shown passing through a hole in pipe section 16 and connected to ground. This is shown for illustrative purposes only. In the preferred embodiment line 24 is actually welded to the interior of pipe section 16. Pipe section 24, being electrically conductive and threaded into other pipes, provides the ground needed and desired.

It should be noted that the diameter of about the upper one-third of cylinder 30 is slightly larger than the lower two-thirds. This upper diameter is about 5% larger than the lower diameter of cylinder 30. The purpose of this slight increase in diameter is to allow a more accessible flowpath for liquid to pass from the interior of pipe cross 14 to the bottom of cylinder 30 when passng between the walls of cylinder 30 and piston 44. This liquid flow will be further elaborated upon below.

Piston 44 is loosely fitted in cylinder 30. It is made of ISP plastic so that at least its external surface will be electrically non-conductive. Its diameter is about 95% of the diameter of the lower portion of cylinder 30. It passes into pipe cross 14 and cylinder 30 through a sealed fitting 46 screwed into the top of pipe cross 14. It is supported and reciprocated by means which are part of the mechanical drive package 11. Piston 44 is reciprocated at a slow frequency of about four cycles per second.

The operation of this apparatus is as follows. Mildly conductive liquid containing non-conductive particles, the electric charge conditions of which is desired to be continuously monitored, is flowed through pipe cross 14 from an external pipe 25. Piston 44 is reciprocated at about four cycles per second by an electric motor driven cam (not shown) in mechanical drive system 11. As the liquid flows over the top of cylinder 30 it is forced in and out of cylinder 30 by the combined action of gravity and hydraulic forces caused by the reciprocating piston 44. Liquid from this flow is forced at a relative high pressure and velocity in and out of the small open annulas 48 located between piston 44 and cylinder 30. Hence, this liquid necessarily flows past new guard electrode 42 and sensing electrode 40, and it necessarily contacts sensing electrode 38. This flow causes what is referred to as a streaming potential to exist between sensing electrodes 38 and 40 and a streaming current to flow between sensing electrodes 38 and 40 and through electrical lead lines 26 and 28. This streaming potential and streaming current are electrical in nature and are a function of the electrical charge on the non-conductive particles in the liquid. The streaming current and potential are proportional to this electric charge condition and alternate at the same frequency as the reciprocating frequency of piston 44. A blocking capacitor, not shown but located in electronic package 12, blocks stray D.C. electric current in leads 26 and 28.

Electronic package 12 processes the alternating current (A.C.) electrical signals so that they become direct current (D.C.) signals which are a function of the desired electrical charge conditions of the liquid.

Electrical conduction lines 55, 56, and 57 connect mechanical package 11 to electrical package 12 so that the A.C. signals caused to be produce in lines 28 and 26 by the reciprocating piston 44 driven by the mechanical drive package 11 can be synchronously demodulated to D.C. electrical signals by the electronics package 12.

Having described the invention, what is claimed is:

1. In an apparatus for determining a function of the electrical charge condition in a flowable liquid media containing electrical charge influencing species, said apparatus having: (a) a substantially vertical tubular flowpath member which has walls which are electrically insulating, which tubular flowpath has an open end at its top and a closed end at its bottom, which closed end is also electrically insulating, and which tubular flowpath is disposed so that it may be substantially filled with said flowable liquid media; (b) a block-like reciprocating element whose outer wall, at least, is electrically insulating and which is disposed in slidable relationship within said flowpath member, said reciprocating element having a transverse cross-section such that it fits adjacent to but spaced from said walls of said flowpath member when it reciprocates in said flowpath member; (c) a pair of spaced sensing electrodes located within said flowpath member, the electrodes being made of the same metal, the first of said sensing electrodes being at least near the closed end of said flowpath member and the second of said sensing electrodes being spaced above the first sensing electrode nearer the open end of said flowpath member with both electrodes so disposed as to be contacted by said flowable liquid media entering or leaving said flowpath member; (d) means for reciprocating said reciprocating element in said flowpath member; (e) means for admitting of said flowable liquid media to said flowpath member; and (f) means coupled to said first and second electrodes to detect and amplify any alternating component of any electrical current flowing betweeen said first and second spaced sensing electrodes; the improvement which comprises:

a guard electrode located inside said tubular flowpath spaced above said second sensing electrode, said second sensing electrode being located below the guard electrode which itself is located at or near the top of said tubular flowpath and above the first sensing electrode which itself is located at or near the bottom of said tubular flowpath with all three electrodes spaced from one another, said guard electrode circling the interior insulating wall of said tubular flowpath means but spaced sufficiently from the block-like reciprocating element to allow free flow of said flowable liquid medium between said guard electrode and said block-like reciprocating element, said guard electrode being electrically grounded and made of the metal as are the said two sensing electrodes, and said guard electrode having a surface and body large enough with respect to the surfaces and bodies of the two sensing electrodes so that its electrical resistivity is negligible with respect to the electrical resistivities of the sensing electrodes in order to shield the sensing electrodes from any galvanic cell-type electrical current which wouold flow through said flowable liquid media between these sensing electrodes and any external metals different in composition from the sensing electrodes in contact with the flowable liquid.

2. The apparatus of claim wherein the electrical resistivity of the screening electrode is no more than 1/5 the electrical resistivity of the second sensing electrode.

3. The apparatus of claim 2 wherein the electrical resistivity of the screening electrode is no more than about 0.1 the electrical resistivity of the second sensing electrode.

* * * * *